United States Patent
Lynn

(10) Patent No.: US 6,600,696 B1
(45) Date of Patent: *Jul. 29, 2003

(54) WOMAN'S ELECTRONIC MONITORING DEVICE

(76) Inventor: Lynn Lynn, 19 West 10th St., Apt. No. 8, New York City, NY (US) 10011

( * ) Notice: Subject to any disclaimer, the term of this patent is extended or adjusted under 35 U.S.C. 154(b) by 1007 days.

This patent is subject to a terminal disclaimer.

(21) Appl. No.: 08/898,340

(22) Filed: Jul. 22, 1997

Related U.S. Application Data

(63) Continuation-in-part of application No. 08/803,624, filed on Feb. 21, 1997, which is a continuation of application No. 08/564,625, filed on Nov. 29, 1995, now Pat. No. 5,606,535.

(51) Int. Cl.[7] .............................. G04B 19/00; A61B 5/00
(52) U.S. Cl. ........................... 368/23; 368/10; 368/107; 600/551
(58) Field of Search .................. 368/10, 223, 107–113, 368/37; 600/551

(56) References Cited

U.S. PATENT DOCUMENTS

| | | | | |
|---|---|---|---|---|
| 3,964,674 A | * | 6/1976 | VanGaast ..................... 368/37 |
| 4,101,962 A | * | 7/1978 | Hakata ........................ 708/161 |
| 4,151,831 A | * | 5/1979 | Lester ......................... 368/10 |
| 4,367,527 A | * | 1/1983 | Desjacques .................. 368/10 |
| 4,443,851 A | * | 4/1984 | Lin ............................ 600/551 |
| 4,488,560 A | * | 12/1984 | Takamura ................... 600/551 |
| 4,527,906 A | * | 7/1985 | Jezbera ........................ 368/107 |
| 5,043,888 A | * | 8/1991 | Uriarte ..................... 364/413.12 |
| 5,058,085 A | * | 10/1991 | Lawler ........................ 368/28 |
| 5,129,057 A | * | 7/1992 | Strope et al. ................. 368/41 |
| 5,515,344 A | * | 5/1996 | Ng ............................. 368/10 |
| 5,606,535 A | * | 2/1997 | Lynn .......................... 368/100 |
| 5,626,133 A | * | 5/1997 | Johnson et al. ............. 128/630 |
| 5,777,905 A | * | 7/1998 | Dowdle et al. ............. 128/738 |
| 5,876,335 A | * | 3/1999 | Handy et al. ............... 600/304 |
| 5,920,871 A | * | 7/1999 | Macri et al. ................ 707/104 |
| 5,928,168 A | * | 7/1999 | Laros, Jr. ................... 600/588 |

* cited by examiner

Primary Examiner—Vit Miska
Assistant Examiner—Jeanne-Marguerita Goodwin
(74) Attorney, Agent, or Firm—De La Rosa & De La Rosa, LLC

(57) ABSTRACT

The present invention is an electronic device or chronometer for use by women of various ages to monitor their menstrual, ovulation and menopausal cycles, as well as their pregnancy. The device displays information relating to a woman's menstrual cycle or pregnancy readily useful to the woman, including the dates of her last and next menstrual cycles, the number of days that have elapsed since the last menstrual cycle, and the next peak ovulation day. If desired, the day(s) a woman expects PMS can also be displayed, such as for those who severely experience the associated symptoms. With respect to pregnancy, the date of conception, the baby's probable due date, and weeks into the pregnancy, among other things, can be displayed.

21 Claims, 10 Drawing Sheets

WOMAN'S ELECTRONIC MONITORING DEVICE

CROSS-REFERENCE TO RELATED APPLICATIONS

This is a continuation-in-part of U.S. patent application Ser. No. 08/803,624, filed Feb. 21, 1997, which is a continuation of U.S. patent application Ser. No. 08/564, 625, entitled "Digital Menstrual Wristwatch," filed on Nov. 29, 1995, issued as U.S. Pat. No. 5,606,535 on Feb. 25, 1997, which are incorporated herein by reference.

TECHNICAL FIELD

The present invention relates generally to menstrual and pregnancy monitors, and more particularly, to digital wristwatches and electronic devices for monitoring women's menstrual, ovulation, and menopausal cycles, and pregnancy.

BACKGROUND OF THE INVENTION

It is well known in the art that a woman's menstrual cycle occurs approximately once a month. For obvious reasons, women monitor the number of days that has passed since their last menstrual cycle or so-called "menses." Indeed, most women, if not all, mark off a fixed number of days from their last menstrual cycle on a calendar to determine when their next period is due. While this method is simple and inexpensive, it also has a number of drawbacks. First, a woman must remember the date of her last menstrual cycle. Second, if a woman incorrectly counts the number of days from her last cycle, she will also make a mistake when her next menstrual cycle or period is due. Third, women who monitor their ovulation, such as for birth control or fertility, can likewise incorrectly count the number of days, and thereby erroneously time the period during which to abstain from or engage in sexual intercourse. Similarly, using this latter method, women can also make a mistake about when to expect pre-menstrual syndrome (PMS), which occurs several days before and after a woman's period.

In the prior art, various attempts have been made for monitoring a woman's menstrual cycle. Most notably, U.S. Pat. No. 4,527,906 to Jezbera discloses a digital watch module that only displays the number of days that have passed since the start of a woman's last menstrual cycle. One primary drawback of the foregoing prior art, however, is its inability, among other things, to display information relating to a woman's menstrual cycle in a manner that is readily useful to a woman. For example, from the displayed information of Jezbera, a woman must still use, for example, a calendar to determine the dates of her last and next menstrual cycles, as well as the dates of her ovulation and pre-menstrual syndrome.

Another drawback in the prior art is its inability to automatically monitor for variations in a woman's cycle. This is especially important inasmuch as women's cycles vary by an average of about seven to thirteen days for peak reproductive years and by even a greater amount for girls in their teens and women approaching menopause.

Furthermore, prior art devices used to calculate a baby's probable due date, among other things, are outdated and readily not useful.

SUMMARY OF THE INVENTION

An object of the present invention, therefore, is to provide an electronic device or chronometer for use by women of various ages to monitor their menstrual, ovulation and menopausal cycles, as well as their pregnancy. More specifically, an object of the present invention is to display information relating to a woman's menstrual cycle and pregnancy that is readily useful to the woman, including the dates of the last and next menstrual cycles, the number of days that have elapsed since the last menstrual cycle, and date of the next ovulation. If desired, the day(s) a woman expects PMS can also be displayed, such as for those who severely experience the associated symptoms. With respect to pregnancy, the probable date of conception, the baby's probable due date, and weeks into the pregnancy, among other things, can be displayed.

A further object of the invention is to automatically monitor for variations in the woman's menstrual cycle, compared to, for example, the actual number of days in her menstrual cycles from previous months.

A further object of the present invention is to provide such a display in conjunction with the current time, day, month and year as well as in conjunction with the display of a standard calendar.

A further object of the present invention is to provide alarms to the woman, programmable one to several days before the start of the menstrual cycle or during the pregnancy, so as to alert the woman that she is within a target range, either relating to ovulation, pre-menstrual syndrome or fetal development.

These and other objects of the present invention are achieved by arranging display windows on the face of a digital wristwatch or display device, which windows are programmable to display the date of the last menstrual cycle, the date of the next menstrual cycle, the number of days since the last menstrual cycle and the date(s) of ovulation. Alternatively, the windows are programmable, if applicable, to display the probable date of conception, the baby's probable due date, and number of weeks into the pregnancy.

In a preferred embodiment, the present invention is a microprocessor-based watch or electronic device responsive to inputs from a user, including the date of her last menstrual cycle and the number of days in the woman's menstrual cycle. In response to such inputs, the microprocessor automatically calculates or estimates the woman's ovulation day(s) and the date of her next menstrual cycle for the purpose of displaying such information to the woman. Alternatively, such information may be used to calculate, if the woman is pregnant, the probable date of conception, the age of gestation, and the baby's probable due date.

Also, the preferred embodiment of the invention includes a look-up table or memory which stores information about a woman's previous menstrual cycles which may be used in determining the date of the woman's next menstrual cycle or ovulation day(s). Also, such prior menstrual history may be used to account or monitor for variations in a woman's menstrual cycle. Furthermore, such information may be retrieved and used for medical diagnostics, if the woman later becomes ill.

In the preferred embodiment, an annular portion of the display may be segmented into equally spaced divisions and used to visually indicate the number of days that have passed since the last menstrual cycle began.

BRIEF DESCRIPTION OF THE DRAWING

Other objects, features and advantages of the invention will become apparent from the following description, together with the accompanying drawings in which like elements are labeled similarly and in which.

DETAILED DESCRIPTION

Without any loss of generality or applicability for the principles of the present invention, the embodiments below herein are directed to a digital wristwatch. It should be understood, however, that the present invention is equally applicable to other types of chronometers, such as clocks or personal computers that function as chronometers.

Figure 1:
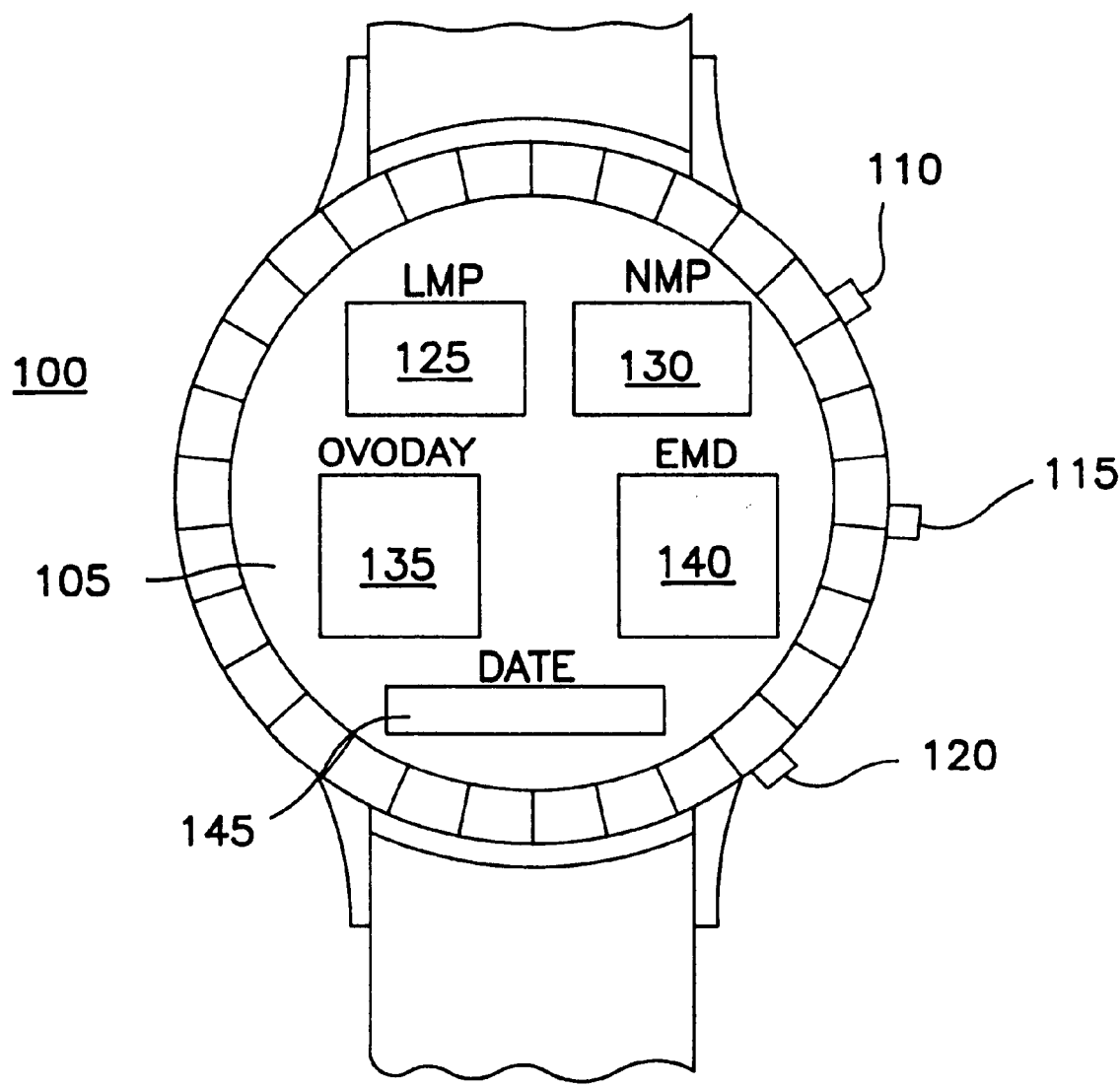
FIG. 1 is a plan view of a digital menstrual wristwatch in accordance with the principles of the invention.

The overall operation of the digital menstrual watch of the present invention may be most easily understood by first referring to FIGS. 1–4. Referring to FIG. 1 there is shown a digital menstrual wristwatch 100 having a LCD face 105, pushbuttons 110, 115, 120, and display windows 125, 130, 135, 140 and 145. Display windows 125, 130, 135, 140 and 145 display the date of a woman's last menstrual period ("LMP"), the date of a woman's next menstrual period ("NMP"), the expected peak ovulation day ("Ovoday") and the number of days that have elapsed since the beginning of the last menstrual period ("EMD"), and the current time and day, respectively. The display windows may be reset to display corresponding information about last month's menstrual cycle when pushbutton 110 is depressed once, and about the month prior to that when depressed twice, and so on.

Figure 2:
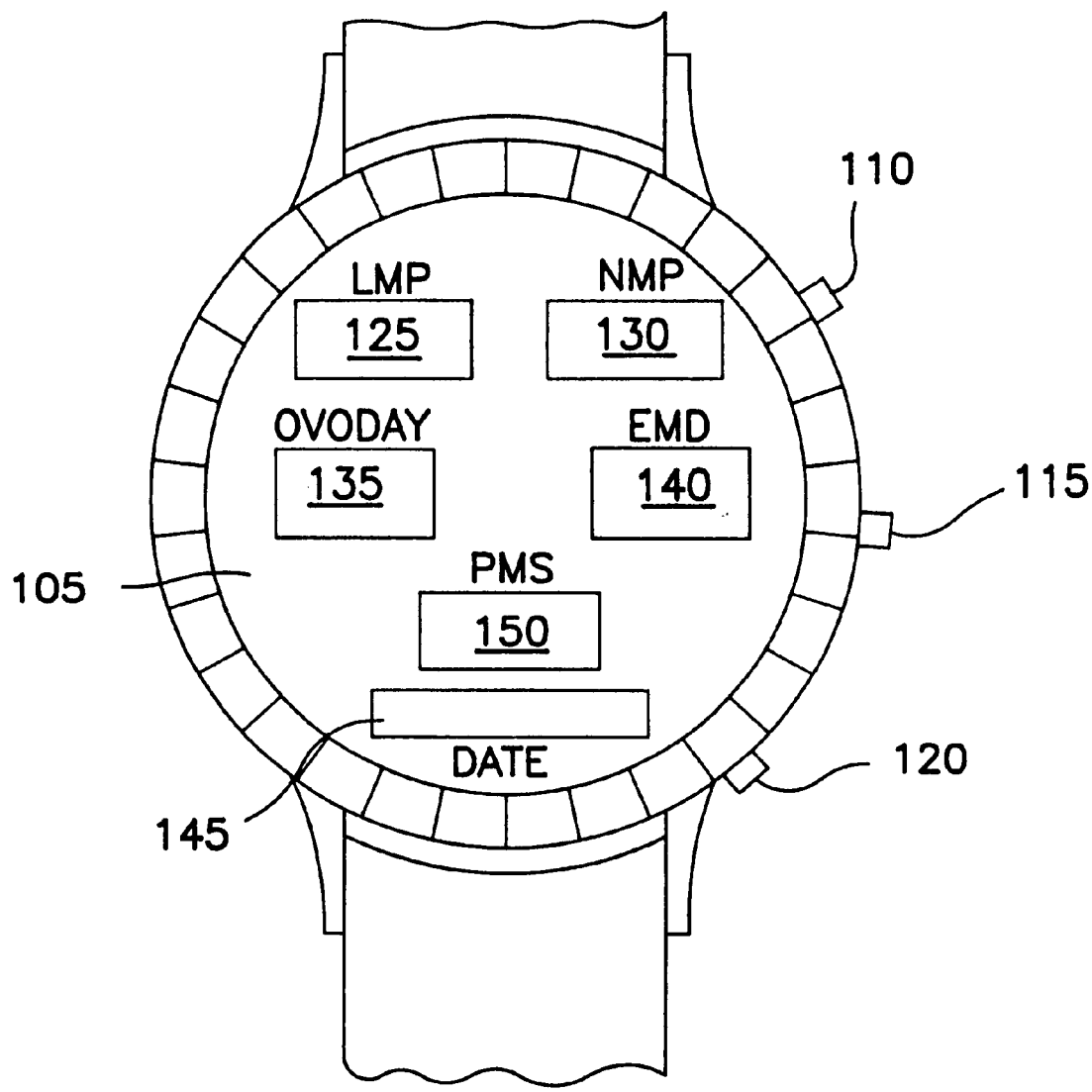
FIG. 2 is a plan view of an alternative embodiment of the present invention.

If desired, the day(s) a woman expects to experience PMS can also be displayed. Referring to FIG. 2, shown there is a display window 150 which indicates the day a woman expects to experience PMS. This day may be programmable from one to several days before the woman's next menstrual cycle. This feature is particularly important for those women who severely experience the associated symptoms of PMS.

Figure 3:
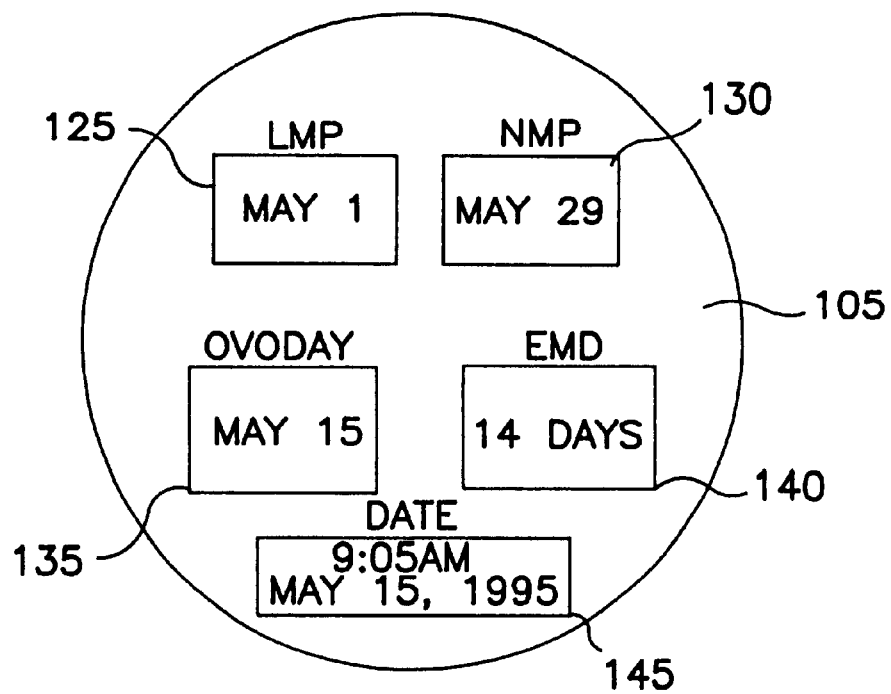
FIG. 3 is an illustrative view of the display of FIG. 1 as it would appear on May 1, 1995.
Figure 4:
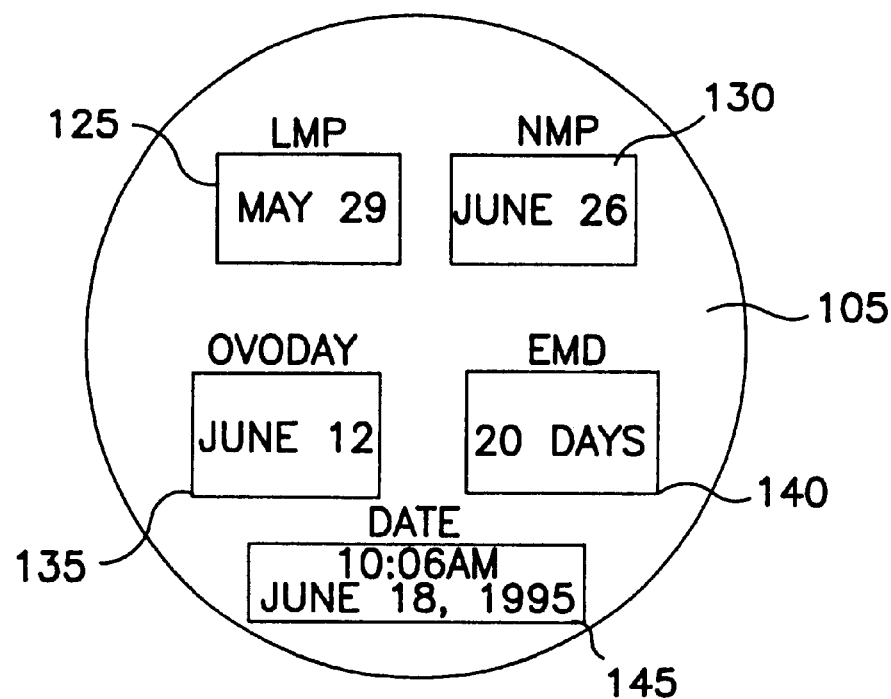
FIG. 4 is an illustrative view of the display of FIG. 1 as it would appear on Jun. 28, 1995.

FIGS. 3 and 4 show how the display windows would appear on May 15, 1995 and Jun. 18, 1995, respectively. As shown in FIG. 3, if a woman's last menstrual cycle was on May 1, 1995 display window 130 labeled "NMP" would display May 29, which is 28 days after the last menstrual cycle or period. It should be understood that on initial use, a woman must first enter the day of her menstrual cycle. In this case, the woman has entered "May 1."

Display window 140 labeled "EMD" would display "14 days" inasmuch as that many days have elapsed since the last menstrual cycle or period. In addition, the current day (May 15, 1995) and time (9:05 a.m.) would be displayed in time/day display window 145. Also, display window 135 would display the peak ovulation day, in this case "May 15" which is 14 days prior to the next menstrual period. Also, a range of dates may be displayed inasmuch as ovulation actually occurs a few days before and following the peak ovulation day.

Alternatively, the current day may be displayed in a standard calendar format with the days corresponding to "LMP," "NMP," and "Ovoday" either boxed or highlighted.

The display windows are updated once a day at the end of each day. For example, on Jun. 18, 1995, several days after the next menstrual cycle had ended, the display windows would appear as shown in FIG. 4. The "LMP" display window 125 would now display "May 29" rather than "May 1". Likewise, the other display windows would have been updated, with "NMP" display window 130 now displaying "June 26" and "Ovoday" display window 135 displaying "June 12". Since today would be Jun. 18, 1995, "EMD" display window 140 would display "20 days." This updating would be done automatically without the intervention of the user.

Inasmuch as menstrual wristwatch 100 cannot determine whether the woman's menstrual cycle occurred on time or on the "NMP" day, such information must be entered by the woman herself. Preferably, this can be done so by the woman simultaneously depressing pushbuttons 110 and 115 on the day menstruation starts. An audible tone may be used as a confirmatory signal that the date has been entered. In this manner, "LMP" display window 125 will subsequently display the actual day the woman had her last menstrual cycle. Likewise, simultaneously depressing pushbuttons 115 and 120 may be used to indicate the occurrence of ovulation.

In above instance, digital menstrual wristwatch 100 initially defaults to a 28-day menstrual cycle and a peak ovulation day occurring 14 days prior to the next menstrual period. Most women's menstrual cycles, however, deviate from those norms. Under such circumstances, when the digital wristwatch is first used, a woman will wish to directly adjust these default values to reflect her particular menstrual cycle. In that case, a woman will depress pushbutton 115 to place menstrual wristwatch 100 in a "setting" mode wherein the default value of the menstrual cycle (28 days) is displayed. By pressing either pushbutton 110 or pushbutton 120 a desired number of times, that default value can be either incremented or decremented, respectively. Once set, pushbutton 115 is depressed again and the default value for the ovulation day (14 days) is then displayed. Similarly, depressing pushbutton 110 or pushbutton 120 increments or decrements, respectively, the default value to suit the particular user. In this manner, the default values within the menstrual wristwatch can be set whenever a woman desires to do so. In a similar manner, a woman may press pushbutton 115 a third time to set the current day of the week, a fourth time to set the month, a fifth time to set the year and a sixth time to set the time (hour, minute, second).

As discussed above herein, a woman on the actual days of ovulation and menstruation confirms their occurrences by simultaneously depressing two pushbuttons. In response to the depression of the pushbuttons, the actual dates corresponding to the onset of menstruation or ovulation are stored in memory, such as in the form of a look-up table. In this manner, the digital menstrual wristwatch of the present invention accumulates the actual dates of menstruation and ovulation on a month-to-month basis. Importantly, the stored menstrual and ovulation dates provide a baseline from which to later change the menstrual data used to estimate the woman's next menstrual cycle or ovulation day(s). This latter menstrual data includes the number of days in the woman's menstrual cycle and the number of days prior to the next menstrual cycle during which ovulation occurs. That is, the woman's prior menstrual history may be used to account or monitor for variations in her menstrual cycle.

For example, at the end of the woman's next menstrual cycle, the device calculates for a predetermined number of previous months, the average number of days in the woman's previous menstrual cycles. This average may then be used to estimate or calculate the date of the woman's next menstrual cycle.

Referring to the table below, if a woman's last menstrual cycle was on May 1, 1995 (Month No. 0), the "NMP" display window would initially display May 29. This is so because the wristwatch uses by default a 28-day cycle, unless changed by the woman. In the first month, however, the woman did not get her period until May 27, two days early of the calculated "NMP" day. At the end of the day on May 27, the display windows are updated. The "LMP" display window now indicates the actual day of the woman's last menstrual cycle, that is May 27. Inasmuch as the average number of days in the woman's menstrual cycle for the previous months is 27 days [(26 days+28 days)/2], the "NMP" window displays "June 27" which is 27 days after the last actual menstrual cycle.

In the following month, the woman's menstrual cycle likewise was not on time, beginning on June 25. That is, 29 rather than 27 days after the last actual menstrual cycle. For the then previous months, the average number of days in the menstrual cycles is now 27.6 days [(28 days+29 days+27 days)/3]. For the remaining four months, with the woman's menstrual beginning on July 23, August 17, September 7 and November 4, the corresponding number of days in the menstrual cycles are 29, 26, 24, 27 and 28 days, respectively. Accordingly, the average number of days in the woman's menstrual cycle for the then previous months are "27.25," "26.6," "26.6" and "26.8" days.

To estimate or calculate the day of the next menstrual cycle, the corresponding average number of days is added to the day of the woman's last menstrual cycle. In this case, those averages yield the following dates for the woman's next menstrual cycles: "August 17" (27.25 day cycle); "September 9" (26.6 day cycle); "October 6" (26.6 day cycle); and "November 4" (26.8 day cycle).

| Month No. | Days in Menstrual Cycle | Average Days in Menstrual Cycle For Previous Months | Next Menstrual Cycle | Last Menstrual Cycle |
| --- | --- | --- | --- | --- |
| 0 | 28 (Default) | 28 (Default) | May 29 | May 1 |
| 1 | 26 | 27 | June 23 | May 27 |
| 2 | 29 | 27.6 | July 23 | June 25 |
| 3 | 26 | 27.25 | Aug. 17 | July 21 |
| 4 | 24 | 26.6 | Sept. 9 | Aug. 14 |
| 5 | 27 | 26.6 | Oct. 6 | Sept. 10 |
| 6 | 28 | 26.8 | Nov. 4 | Oct. 8 |

Over time, irregularities in the woman's menstrual cycle will not abruptly, but gradually offset the number of days between the "LMP" and "NMP" so as more properly estimate when the woman can expect to get her period. Advantageously, a woman need not monitor how many days her cycle is off inasmuch as it is now performed automatically so long as she simply depresses the pushbuttons on the wristwatch to indicate the start of her menstrual cycle.

Alternatively, the device may calculate or estimate the woman's next menstrual cycle by always using a fixed number of days from the last menstrual cycle. This latter fixed number of days may be set by the woman. Or, the device may use simply the number of days in the woman's last menstrual cycle so as to more properly estimate the day of the woman's next menstrual period. Regardless of the method, it should be understood that each method only provides an estimate as to when a woman may expect to have her next menstrual cycle. None of the methods can actually predict when a woman will have her period inasmuch as there are too many unknown variables.

Similarly, the above methodologies may be used to estimate the woman's next peak ovulation day, which normally occurs 14 days before her next menstrual cycle. The peak ovulation day is displayed in display window 135. Alternatively, the days a woman is ovulating may be displayed, which typically occurs three days before and four days following the peak ovulation day. It should be understood that the onset of pre-menstrual syndrome may also be determined and displayed in a similar manner in display window 150.

Accordingly, the wristwatch of the present invention can be programmed to account or monitor for variations in a woman's menstrual cycle based on her past menstrual history. Various other programming techniques for effecting this latter methodology are well known in the art and may include the use of other statistical techniques, such as weight averaging, standard deviation and the like. It is also contemplated that artificial intelligence or logic called "fuzzy-logic" may also be used.

Figure 5:
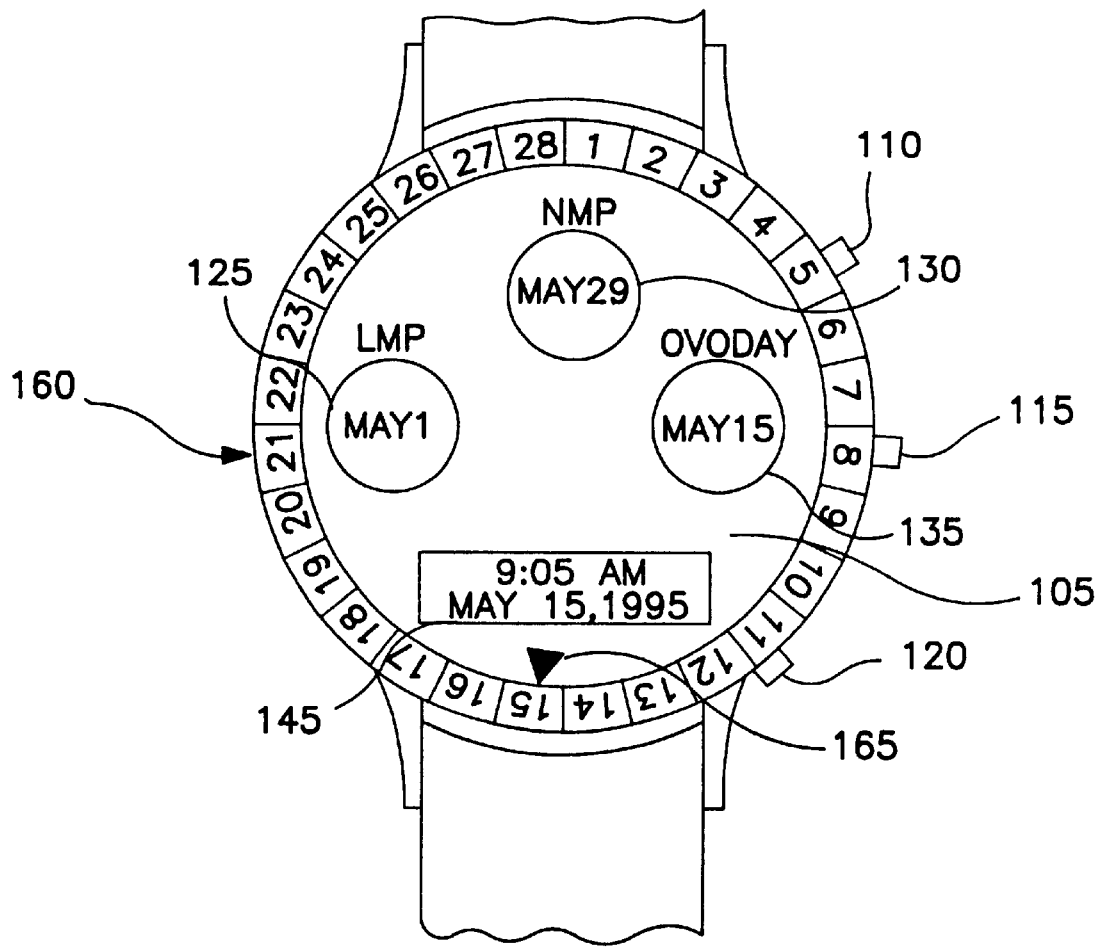
FIG. 5 is a plan view of another alternative embodiment of the present invention.

Referring now to FIG. 5, there is illustrated an alternative preferred embodiment of the present invention which is similar to the embodiment of FIG. 1, but differs from that embodiment in that an annular display portion 160 on the face of the watch is segmented into equally spaced numbered divisions. These divisions are used to visually indicate the number of days that have passed since the last menstrual cycle began, each division corresponding to an elapsed day. A display pointer 165 is positioned adjacent to the number of days since the woman's last menstrual cycle. It should be understood that other pointer or indicator means may be used. For example, the numbered divisions may be highlighted or blacken in the appropriate manner.

Although annular display 160 has only 28 days displayed, should the woman change the default setting, a corresponding number of divisions will then also be displayed. That is, if her menstrual cycle has 30 days, then 30 divisions would be displayed. Should the woman's menstrual cycle occur more than 28 days after her last cycle, the pointer simply wraps around, restarting on day number one. In this manner, a woman can readily observe how many days she is late.

An additional feature of the present invention is its programmable alarm capability. A woman may, if she desires, program the wristwatch of the present invention to alert her that she is within a given number of days ("target range") prior to menstruation. Similarly, other alarms may be programmed with respect to ovulation, pre-menstrual syndrome or medication. For example, menopause for some women is eased with medication taken in cycles, e.g., 14 days on and then 14 days off. Accordingly, the present invention may be programmed to remind the woman at the beginning or ending phase of her medication or at any other interval. Preferably, the alarm(s) are audible to the user, such as a sound, voice or word, either alarming on a single day or on a number of days prior to menstruation, ovulation, pre-menstrual syndrome and/or medication. Of course, to indicate which alarm it is, a different sound or word may be used for each.

Furthermore, the present invention may be programmed to keep a log of the length of a woman's menstrual cycle, particularly useful for those women experiencing menopause. A woman may notate for each month the severity of her menstrual flow with the symbols S (scant), L (light), M (Medium) and H (Heavy), as well as indicate the length of her menstruation. For example, a typical archive may be displayed as follows:

Feb 2 (72) 5M
Apr 15 (84) 2L
Jul 19 (28) 7H wherein the number preceding the symbols S, L, M and H indicate the number of days of menstruation. The numbers in parentheses indicate the number of days between her periods. It is contemplated that this archival or almanac information can be displayed on the display portion of the watch. Also, with some woman over 40 having difficulty seeing small letters, it is contemplated that the display of the present invention in some embodiments may be designed with larger letters, as well as backlighting.

Figure 6:
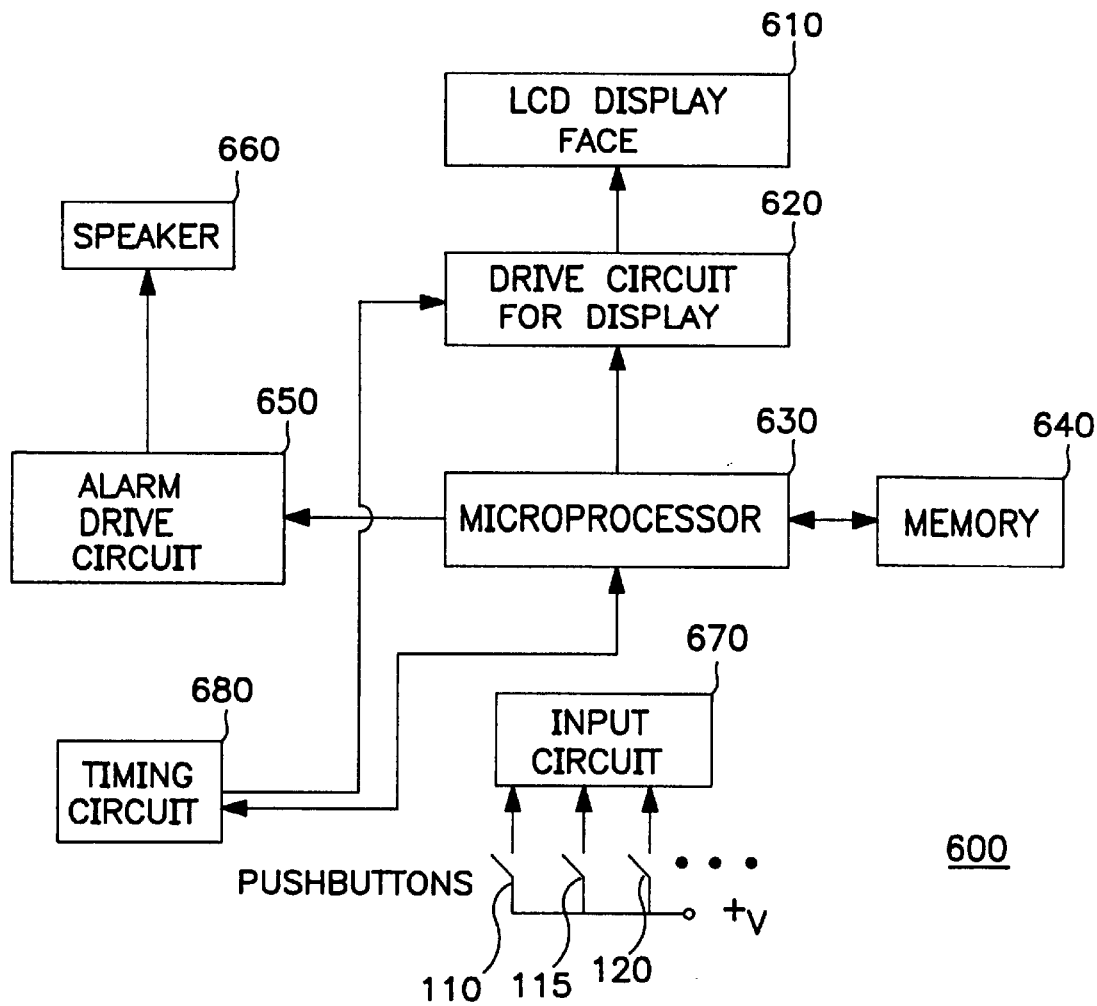
FIG. 6 is a functional block diagram illustrating the operation of the present invention.

FIG. 6 shows an illustrative functional block diagram of a control circuitry 600 of the invention. In this embodiment, control circuitry 600 includes eight distinct elements; LCD display face 610, display drive circuit 620, microprocessor 630, memory 640, alarm drive circuit 650, speaker 660, input circuit 670 and timing circuit 680. It should be understood, however, that the electrical circuits performing the functions of these elements need not be discrete and may be integrated in any manner, provided that the eight basic functions of these elements are performed.

The display function is performed by LCD display face 610 which operates in response to signals from drive circuit 620. LCD display face 610 comprises, for example, a dot matrix panel for at least displaying in predefined portions or windows thereof the date of the woman's last menstrual cycle, the date of the woman's next menstrual cycle, the number of days since the woman's last menstrual cycle and the current day and time. LCD display 610 may be in the shape of a circle, rectangle, or square.

More specifically, control circuitry 600 uses a microprocessor 630 having random access memory (RAM) 640 and internal hardware logic. Under program control, microprocessor 630 provides signals to drive circuit 620 so as to have displayed the menstrual data as discussed above in relation to FIGS. 3 through 4. That is, specific dots of the LCD display face are selectively activated by drive circuit 620 so as to display the appropriate data in display windows 125, 130, 135, 140, 145, 150 and 160. The display windows may be generated likewise in the shape of a circle, rectangle or square. Those skilled in the art will readily note that such menstrual data may alternatively be displayed, for example, using 7-segment LED displays.

It should be understood that microprocessor 630 includes such hardware as a central processing unit, program and random access memories, timing and control circuitry, input/output (I/O) interface devices and other digital subsystems necessary to the operation of the central processing unit. Also, those skilled in the art will readily note that the menstrual wristwatch of the present invention may be completely implemented using analog circuitry.

The digital wristwatch operates in accordance with a program whose methodology of operation is set forth above herein for displaying the above menstrual information or data. This program can be stored in conventional random-access-memory or in a preprogramed chip, such as EPROM or EEPROM. In particular, the program is made up of a number of instructions that are in coded binary format understood by the microprocessor, so that the program can tell the microprocessor how to calculate, for example, the date of the woman's next menstrual cycle, the number of days since the woman's last menstrual cycle, and the expected date(s) of ovulation.

Control circuitry 600 is provided with timing circuit 680, preferably having a quartz crystal oscillator. Timing circuit 680 generates digital signals to drive circuit 620 corresponding to the current day, time, month and year. For example, timing circuit 680 may be a standard watch module. Timing circuit 680 updates the display, for example, once every hundredth of a second, so as to perform the clock function needed to keep track of time. These digital signals are also provided to microprocessor 630 so that it too knows the time and day. This time data is stored in RAM by the microprocessor and is updated on a need-to-basis.

The inputs to the microprocessor are entered through input circuit 670 and pushbutton 110, 115, 120. Input circuit 670 may use standard buffers and encoders, which are well known in the art. Preferably, whenever any of the pushbuttons are depressed, an interrupt signal goes to microprocessor 630, causing it to execute the appropriate interrupt routine necessary to read the inputs from the pushbuttons.

The function of alarm drive circuit 650 is, in response to digital signals from microprocessor 630, to generate audible tones at different frequencies via a speaker 660. These tones indicate different times within a woman's menstrual cycle in relationship to a woman's menstruation, ovulation or PMS. The operations of such alarm drive circuits are well known in the art and accordingly will not be discussed here for the sake of clarity.

Figure 7:
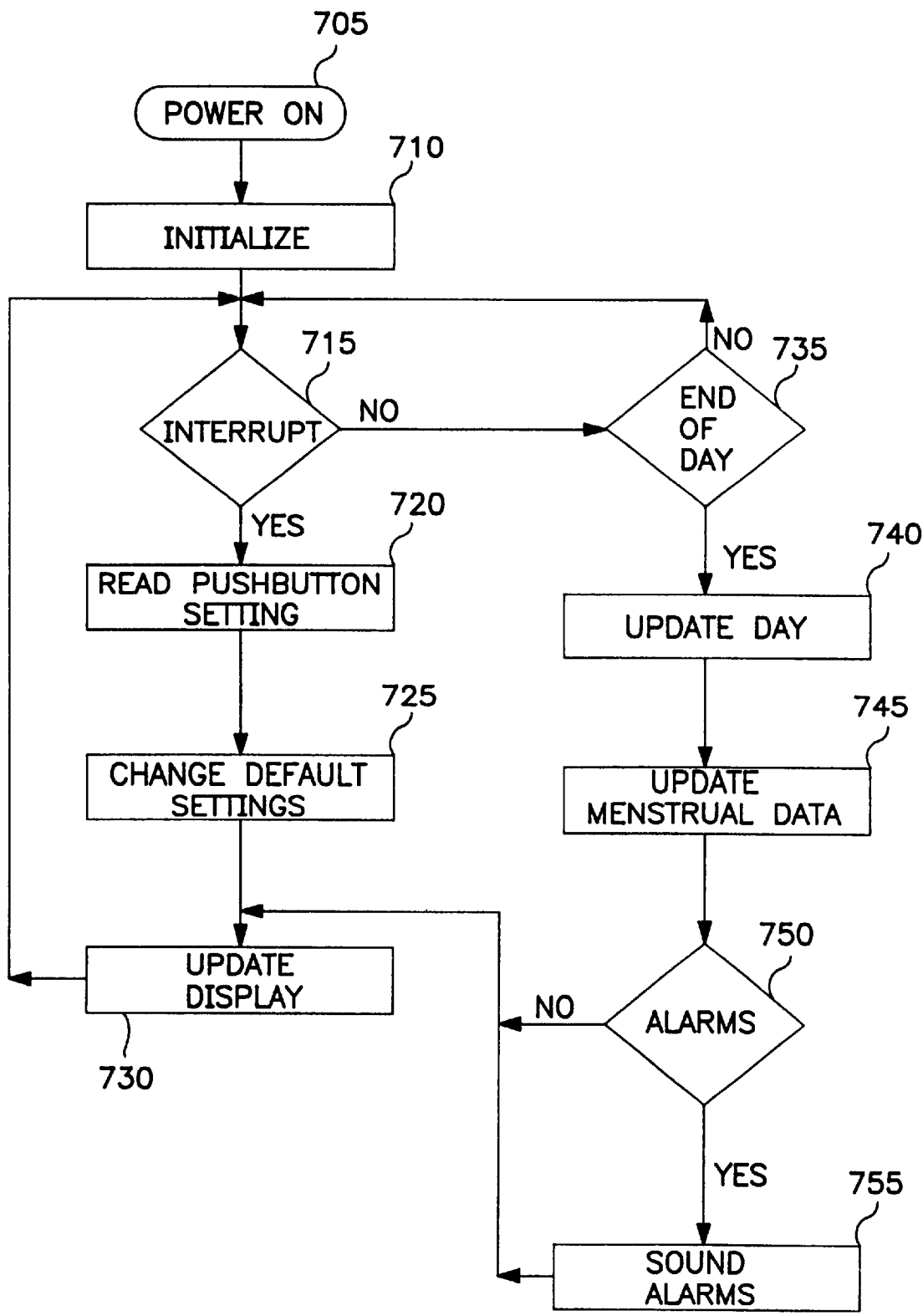
FIG. 7 is a flow chart of an illustrative program for the microprocessor of FIG. 6.

The operation of microprocessor 630 of FIG. 6 can be understood more clearly from the flow chart of FIG. 7, together with the following discussion. As shown in FIG. 7, the operation of the microprocessor 630 is centered, in part, around the detection of an interrupt in decision block 715. It is necessary, however, that a portion of the control program stored in memory provides a routine for initializing microprocessor 630 when power is first applied. Therefore block 705 indicates a power on condition, and block 710 indicates that the microprocessor is initialized. In block 710, a routine is executed which initializes a number of registers in memory. Some of these registers correspond, for example, to the default settings for the number of days in a woman menstrual cycle, the number of days prior to the next menstrual that ovulation occurs and a default setting for the woman's last menstrual cycle (day, time, month and year). Other registers will also be initialized relating to alarm settings discussed above herein. Once the initializing has been completed, it need not be repeated until the microprocessor is turned off and then turned on again, such as when there is a loss of power due to battery failure. To alleviate this problem, however, it is contemplated that the menstrual wristwatch of the present invention includes a backup battery.

Decision block 715 tests the interrupt line setting to the microprocessor to determine whether any of the pushbuttons have been depressed and hence have send out an interrupt request. Should the pushbuttons be repeatably depressed, an appropriate interrupt may be generated to indicate so. If so, the microprocessor reads the pushbutton settings, and accordingly changes the default settings, as discussed above and shown in blocks 720 and 725. For example, the number of days in the woman's menstrual cycle may have been changed or the date of the woman's last menstrual cycle set for the first time. If the user, however, sets the current time, day, month and year, the microprocessor will accordingly instruct the timing circuit to do likewise.

After testing for an interrupt signal, the microprocessor will check in block 730 to see if it is the end of the day. If so, the microprocessor updates in block 735 its internal registers that keep track of the current day. When this has been completed, the microprocessor updates the woman's menstrual data, as shown in block 740. Unless the woman has indicated that menstruation has started, the number of days displayed since her last menstrual cycle is incremented by one. If the woman, however, has indicated so, the "LMP" display window is replaced with the actual date of her menstruation. Moreover, the microprocessor, using, for example, the average number of days in her menstrual cycles for the prior months, determines the date of her next menstrual cycle as discussed above herein. Similarly, information relating to the woman's ovulation and, if displayed, information relating to her PMS is updated.

At the end or the start of each day, the microprocessor checks in block 750 for alarm settings. If the current day is equal to or within a programmable number of days to any of the alarm setting set by the woman, the microprocessor causes an audible tone to be heard by the woman at a predetermined time of day.

When these routines are completed, the microprocessor proceeds to update the information on the LCD display face. This step consists of sending the appropriate data to the drive circuit so as to permit the drive circuit to display the correct menstrual data. Afterward the microprocessor loops back to the beginning so as to start the entire process over again.

Over several months, the menstrual wristwatch accumulates menstrual data which is stored in memory. It is contemplated that the digital menstrual wristwatch of the present invention may be interfaced with an external computer like the IBM PC or the Apple Macintosh thru an external port. In this manner, a woman's menstrual data may be downloaded for medical diagnostic purposes, among other things. The wristwatch can also interface with small hand-held pocket computers like those readily available from Texas Instrument, Hewlett Packard, and Casio, among others.

It should be emphasized that the above described flow chart, shown in FIG. 7, is merely one example of how microprocessor 630 may be programmed in order to control LCD display face 610. Similarly, the combination of components shown in FIG. 6 could be changed to meet specific design requirements, such as requirements for additional inputs or different types of displays or timing circuits.

Figure 8:
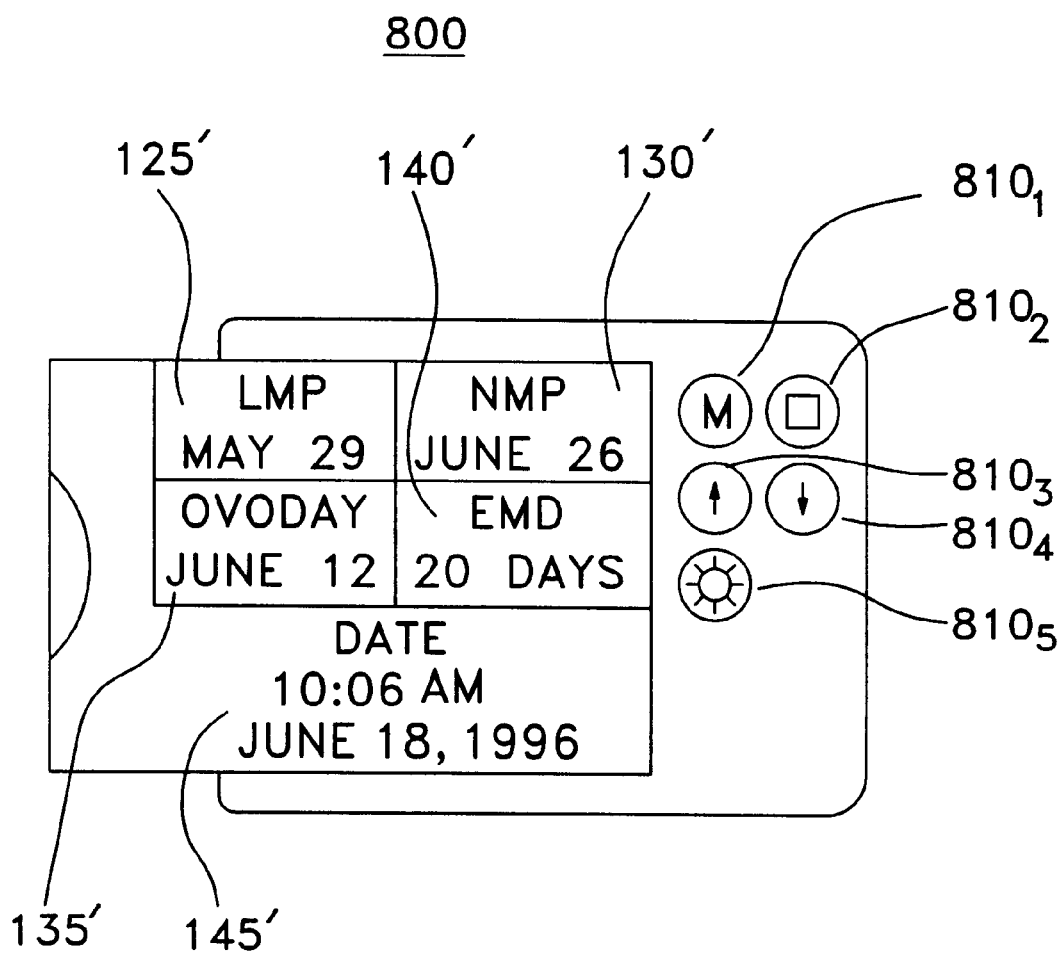
FIG. 8 is a plan view of yet another alternative embodiment of the present invention.

For example, the present invention may be implemented in the form of a self-contained thin display enclosure device 800, as shown in FIG. 8. Display enclosure device 800 is similar to the above embodiments, but uses five keypads rather than three push-buttons to effect programming. Moreover, the display enclosure device is conveniently sized for insertion into a purse or provided in a less miniaturized format resembling a conventional hand-held or pocket size calculator or other similar device.

Likewise, display enclosure device 800 includes an internal microprocessor, a memory unit, and an externally visible LCD display screen having display windows 125', 130', 135', 140' and 145'. The LCD display screen is capable of displaying both data and graphics. Five keypads 810$_{1-5}$ are used to program and enter data in a menu driven manner into the display enclosure device. Information relating to the woman's menstrual cycle, among other information, can be readily displayed to the woman.

As illustrated in FIG. 8, a woman's last menstrual period ("LMP"), next menstrual period ("NMP"), peak ovulation date ("Ovoday") and elapsed number of days since her last menstrual period ("EMP") can be displayed in display windows 125', 130', 135', and 140', respectively. It should be understood that ovulation occurs approximately for a length of about three days before and four days after the peak ovulation day. As such, the dates a woman is ovulating may be displayed in display window 135' rather than the peak ovulation date. If desired, the current date and time can also be displayed in another display window, such as display window 145', or in another portion of the display face of the device. Any other information as discussed herein above may also be displayed.

Keypads 810$_{1-5}$ are respectively labeled "M" for menu; "☐" for select; "↑" for scroll up; "↓" for scroll down; and "↕" for back light, respectively. When selecting one of these keypads, an audible signal is heard by the user.

The main display screen—consisting of display windows 125', 130', 135', 140' and 145'—can be switched to display a main menu by pressing keypad 810$_1$ ("M") which menu consists of the following submenu:

1. LMP
  2. Cycle Length
  3. Select Alerts
  4. Set Clock
  5. Set Alarm
  6. Archive
  7. LCD Contrast
  8. Default Setting Initially, submenu "1" is highlighted, but by using scroll keypads 810$_4$("↓") and/or 810$_3$("↑"), other submenus may be accordingly highlighted. Pressing keypad 810$_2$ ("☐") selects the highlighted submenu and places the device in that corresponding mode.

To set the date of the woman's last menstrual period (LMP), submenu "1" is selected using keypad 810$_2$ ("☐") which then displays the current LMP date stored in memory. For example, such a display may be shown as:

* LMP *
  1997 JAN 1 (WED)

The year, date and day can be highlighted in sequence by pressing keypad 810$_2$ ("☐") in a sequential fashion. Then using the scroll down keypad 810$_4$ ("↓") and scroll up keypad 810$_3$ ("↑"), each field may be changed accordingly to the correct year, date and day. When set, menu keypad 810$_1$ ("M") may be pressed to exit and return to the main menu.

From the main menu, another submenu can be selected using keypad 810$_2$ ("☐"). Selecting submenu "2" allows the user to change the cycle period which is set to a 28-day default cycle. Initially, the user is displayed with the following display when submenu "2" is selected:

* CYCLE LENGTH *
  28

Using scroll down keypad 810$_3$ ("↓") and scroll up keypad 810$_4$("↑"), the cycle period may be changed to reflect the woman's particular menstrual cycle. Pressing keypad 810$_1$ ("M") returns the user to the main menu. As discussed above herein, the device uses this cycle period to calculate the woman's next menstrual period.

The "Set Alert" submenu or submenu "3" is selected using the scroll down 810$_4$("↓") and scroll up 810$_3$("↑")

keypads in conjunction with select keypad 810₂ ("☐"). When selected, submenu "4" itself consists of another submenu having the following items:

1. Peak Day/OvoAlert
2. Reminder/PMS Alert
3. Late Alert Selecting submenu "1" of the "Set Alert" menu allows the woman to view the mid-cycle date of her menstrual cycle and a range about which she is most likely to be fertile, as illustrated below.

*PEAK DAY*
1997 JAN 14 (WED)
RANGE: JAN 9 TO JAN 19
ALARM: 12:00 PM ON. OFF.

On those days noted in the "Range," the device alerts the woman at the predetermined time indicated on the last line that she is most likely to be fertile. Of course, this alarm may be set "off" using the scroll up and scroll down arrow keypads 810₃("↑"), 810₄ ("↓") in conjunction with select keypad 810₂("☐"). The time at which the woman is alerted may also be changed in a similar manner, if desired.

Selecting submenu "2" of the "Set Alert" menu allows a woman to change the number of days before her next menstrual cycle she will be alerted that she is likely to experience PMS. An illustrative display is shown below:

*REMINDER/PMS ALERT*
4 DAYS BEFORE PMS
1997 JAN 25 (SAT)
ALARM: 12:00 PM ON OFF

Again by using the scroll up and down keypads 810₃ ("↑"), 810₄ ("↓") respectively, along with select keypad 810₂ ("☐"), the woman may set the alarm off or on, as well as set the number of days before her next cycle (second line) and the time at which she is to be alerted (last line). To indicate that the alarm is set, a small icon of a bell may be displayed on the display face of the device.

Selecting submenu "3" of the "Set Alert" menu allows a woman to change the number of days after her next menstrual cycle she will be alerted to being "late," that is missing her period. By default, the device uses 12 days since most pregnancy tests will test positive after that time period, if indeed the woman is pregnant. A typical display may appear as:

*LATE ALERT*
12 DAYS AFTER LMP
1997 Feb 10 (MON)
ALARM: 12:00 PM ON. OFF.

The late alert can be adjusted using any number of days a woman chooses (second line) and may be set off by highlighting the "OFF" legend (last line) and then pressing select keypad 810₂("☐"). Returning to the main menu is effected through main menu keypad 810₁("M").

In a like manner, the current date and time can set by selecting submenu "4" from the main menu. A typical display may look as follows:

*CLOCK*
12:00 PM 12 HOUR
1997 JAN 1 (WED)

Keypad 810₂ ("☐") is used to highlight each field. And, scroll down keypad 810₄ ("↓") and scroll up keypad 810₃ ("↑") used to change its value. When set, keypad 810₂ ("☐") is again pressed. Keypad 810₁ ("M") returns the user to the main menu.

Now referring to submenu "5" of the main menu or the "Set Alarms" submenu, a woman can arbitrarily set an alarm for any time and date, for example, corresponding to a doctor's appointment or the like:

*SET ALARM*
1997 JAN 1 (WED)
12:00 PM
ALARM: ON OFF

Using again keypads 810₂–810₄, the time and date of the alarm may be changed. If desired, the alarm can be turned off by pressing keypad 840₂ ("☐") twice.

Placing the device in submenu "6" or the archive mode displays information on the woman's recorded menstrual cycles, including the actual dates of her last periods, the cycle length, and the duration and amount of menstrual bleeding, as illustrated below:

*ARCHIVE*
FEB 1 97 (29) 5L
MAR 1 97 (27) 4M
MAR 29 (27)

The numbers in parentheses indicate the number of days in the woman's cycle whereas the numbers preceding the symbols S ("Scant), L ("Light"), M (Medium") or H ("Heavy") indicate the duration of menstrual bleeding. The last entry, however, is for the woman's next menstrual cycle and as such is incomplete. Again, using the scroll up and down arrow keypads 810₃, 810₄, a woman may change or modify the displayed information.

Selecting submenu "7" allows the user to change the LCD contrast by pressing the scroll up and down keypads. And, selecting submenu "8" sets the device to its default settings should the settings above have been entered erroneously or accidentally.

In another alternative preferred embodiment, the present invention is likewise a lightweight, portable information display and processing device that is self-contained within a thin enclosure. The device, however, is principally designed for doctors, nurses, midwives and other health professionals to calculate and display information relating to a woman's pregnancy. Likewise, this electronic device may display the current time, day, and date. Also, a full calendar month can be displayed on the display area of the device which may be scrolled forward or backward in a manner well known in the art. In this standard calendar format, it is contemplated that the probable conception date and the baby's probable due date may be either boxed or highlighted.

The baby's probable due date or estimated date of confinement ("EDC") may be predicted by adding nine calendar months and five days to the date of a woman's last menstrual period ("LMP"), after missing an expected menstrual period. Preferably, however, Nagel's rule is used, requiring three months to be subtracted from the LMP and then adding 7 days. One in 20 women will have her child on exactly that day and about two in every five will deliver within one week on either side of it. Like every other aspect of pregnancy the actual duration varies from one individual to the next, but doctors generally agree that variations may well occur of up to about 30 days either way. Pregnancies from 250 to 310 days are considered normal. The probable conception date, however, is usually two weeks after the last menstrual period. Preferably, however, inasmuch as the length of the woman's menstrual cycle is stored, the probable conception date may be estimated by automatically adding to the LMP half the number of days in the woman's menstrual cycle.

Figure 9:
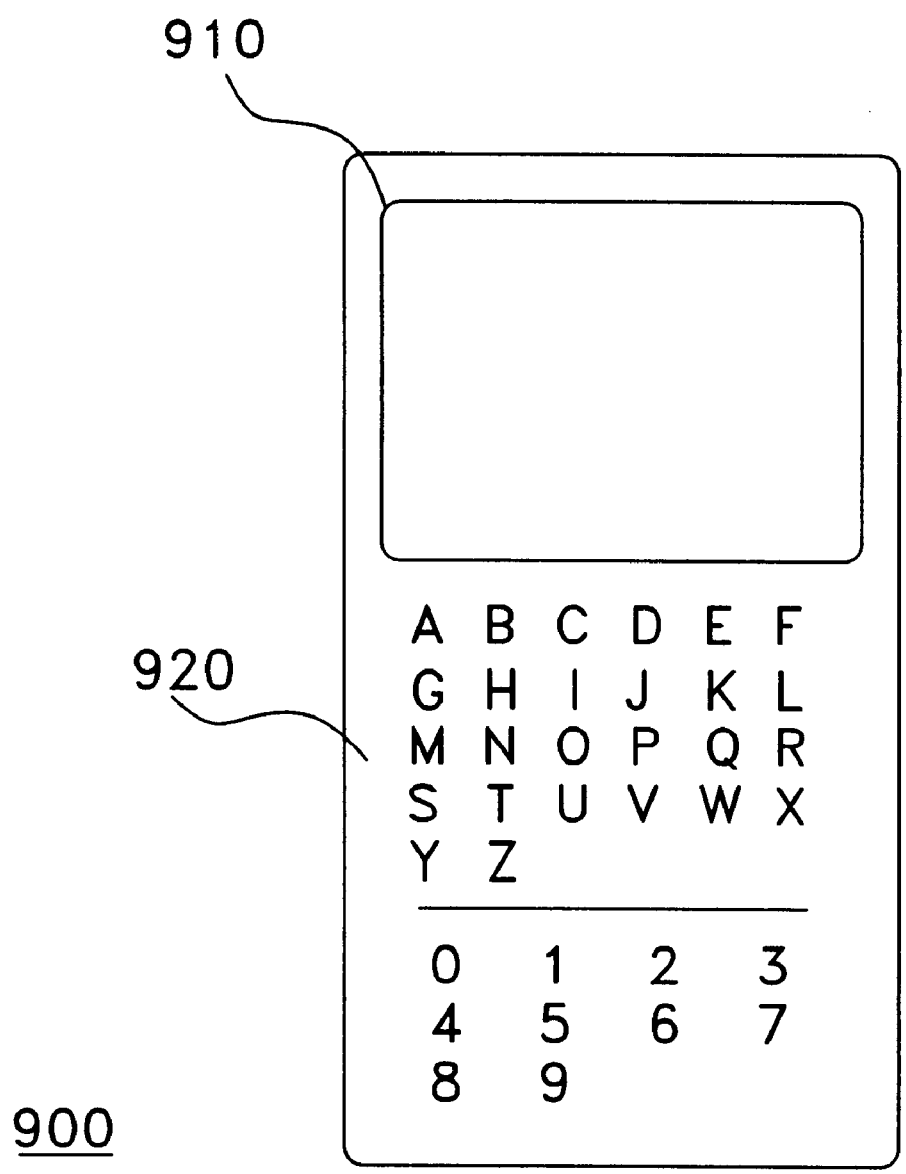
FIG. 9 is a plan view of still yet another embodiment of the present invention useful in calculating a baby's probable due date, probable date of conception and age of gestation.

Referring to FIG. 9, electronic device 900 incorporates an internal microprocessor (not shown), memory unit (not shown), a visible LCD display screen 910, and a keypad 920 used to enter alphanumeric characters. When initially programmed with the date of the woman's last menstrual period and the length of menstrual cycle via keypad 920, electronic device 900 calculates in a manner well known in the art and stores the probable date of the conception; the baby's probable due date or estimated date of confinement ("EDC"); the pregnancy week of the fetus or age of gestation ("AOG"); the beginning dates of the woman's second (13–28 weeks) and third trimesters (29–42 weeks); and the number of weeks remaining in the pregnancy. Along with this information, the current date and time is preferably displayed to the woman.

Importantly, this information is automatically made and updated on the basis of the current date, day and year which is stored in memory and displayed to the user. A user need not count a given number of days or months from her LMP or even need remember the current date. The number of weeks remaining in the woman's pregnancy as well as the current AOG is automatically updated from week to week. Moreover, this information may be stored in memory and associated with the particular name of an individual for later access and retrieval.

Figure 10:
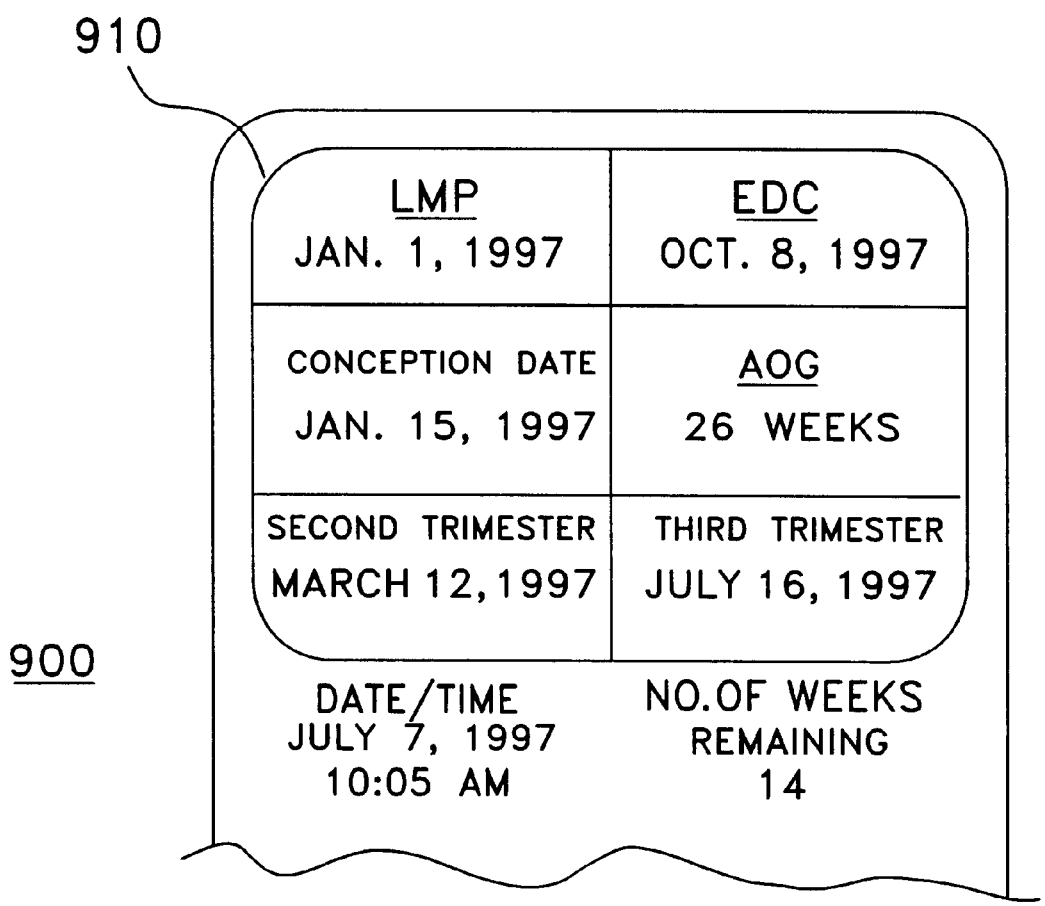
FIG. 10 is an illustrative view of the display of FIG. 9 as it would appear on Jul. 7, 1997.

The pregnancy information is displayed on LCD display screen 910. FIG. 10 shows how the display would appear on Jul. 7, 1997 if a woman's last menstrual cycle was on Jan. 1, 1997. It should be understood that this display format is not unlike the display format relating to the woman's menstrual cycle discussed herein above. Moreover, it should be clearly understood that embedded software in the electronic device implements the algorithm used to calculate the latter information. Importantly, this information may be programmed to be updated automatically without the intervention of the user. This may be readily effected in manner similar to that in the above embodiments. For example, on Jul. 16, 1997 the "AOG" legend would display 27 rather than 26 weeks, since it now a week later. Moreover, it would now indicate that only 13 week are remaining in the pregnancy rather than 14 weeks. Alternatively, the AOG may be displayed in terms of months or days, rather than weeks. Or, the display may indicate the number of weeks remaining in the woman's pregnancy in terms of months or days, which also can be updated on a daily basis.

Additional information may also be displayed, including the date after which all pregnancy tests would tell a woman if she is pregnant, which is generally 40 days after the date of a woman's last menstrual period. Furthermore, the weeks and dates that amniocentesis, CVS testing and the like should be performed—typically, in the 11–17th week—may also be calculated and displayed to the user. Still further, the last day on which a woman can have an abortion can also be displayed. Yet still further, the weeks a woman can expected to feel fetal movement can also be readily displayed, which typically occurs the 18–20th week.

It is also contemplated that fetal weight and height charts may be stored in the form of a look-up table within the memory of electronic device 900.This information is automatically updated as each week progresses. The growth process is not steady or continuous and can be divided into two separate phases. Until the end of the second month, the egg goes through the embryonic phase of development, developing a head, body and internal organs. Thereafter, the embryo grows more rapidly, with its length increasing faster than its weight.

Figure 11:
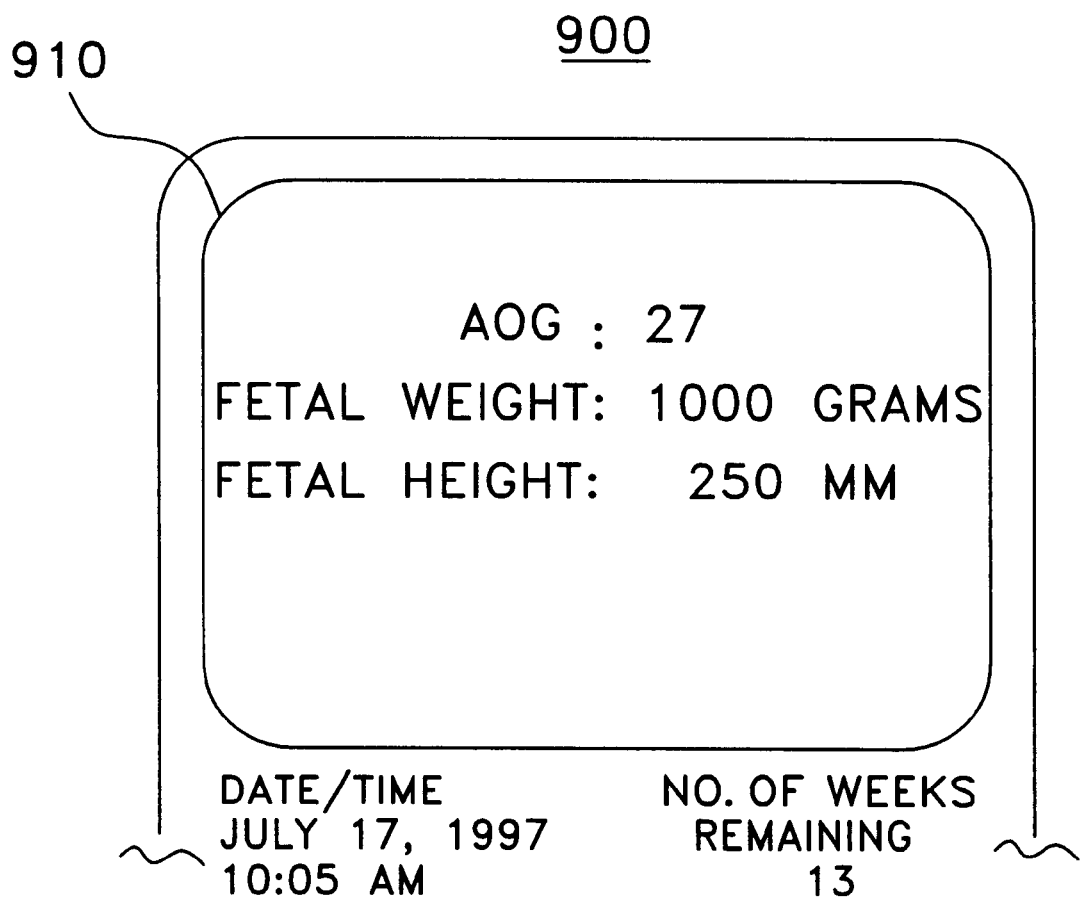
FIG. 11 is another illustrative view of the display of FIG. 9.

If desired, the fetal weight and height corresponding to the current AOG may be displayed on the display face of device 900. FIG. 11 shows how the display would appear on Jul. 17, 1997 if the woman's last menstrual cycle started on Jan. 1, 1997.

Thus, it should be clearly understood that the embodiment herein is merely illustrative of the principles of the invention. Various modifications may be made by those skilled in the art which will embody the principles of the invention and fall within the spirit and the scope thereof.

What is claimed is:

1. A device for monitoring the menstrual cycle of a woman, said device comprising:
   a housing;
   memory means for storing data associated with the woman's menstrual cycle;
   a display disposed on said housing;
   display drive means responsive to said memory means for displaying information associated with the woman's menstrual cycle on said display;
   without user intervention, means for automatically updating from day to day said information associated with the woman's menstrual cycle on the basis of both said menstrual data stored in said memory means and the current date; and
   menu driven means for entering said data associated with the woman's menstrual cycle so as to reflect the woman's particular menstrual cycle.

2. The device of claim 1 wherein said menu driven means includes keypads for changing said data associated with the woman's menstrual cycle.

3. The device of claim 1 wherein said data associated with the woman's menstrual cycle includes the date of the woman's last menstrual cycle and the number of days in the woman's menstrual cycle.

4. The device of claim 1 wherein said different information associated with a woman's menstrual cycle includes the date of the woman's next menstrual period, and the number of days since the woman's last woman's menstrual cycle.

5. The device of claim 1 wherein said different information associated with a woman's menstrual cycle includes the date of a woman's ovulation, and the date a woman expects to experience pre-menstrual syndrome.

6. The device of claim 1 further comprising timing means for generating signals corresponding to the current time and day, and said display drive means further for displaying said current time and day on said display.

7. The device of claim 1 wherein said means for automatically updating includes means for estimating the date of the woman's next menstrual cycle.

8. The device of claim 1 wherein said display includes a plurality of predefined display windows, said information associated with a woman's menstrual cycle being displayed within said display windows.

9. The device of claim 1 further comprising means for alerting the woman at predetermined times within her menstrual cycle.

10. The device of claim 1 wherein said display drive means further concurrently displays said different information associated with a woman's menstrual cycle in conjunction with a standard calendar display.

11. The device of claim 1 wherein said different information associated with the woman's menstrual cycle includes the dates of the woman's last menstrual cycles, the duration of each menstrual cycle, and the amount of menstrual bleeding during each menstrual cycle.

12. A device for displaying information associated with a woman's pregnancy comprising
   a housing;
   a display face on said housing;
   memory means for storing the date of the woman's last menstrual cycle;

means for estimating pregnancy data, including, the probable date of conception, the estimated age of gestation and the estimated date of confinement, and the number of weeks remaining in the woman's pregnancy on the basis of both the date of the woman's last menstrual cycle and the current date;

means for displaying on said display face said pregnancy data; and without user intervention, means for automatically updating from day to day said pregnancy data.

13. The device of claim 12 further comprising means for entering the date of the woman's last menstrual cycle.

14. The device of claim 13 wherein said means for entering includes an alphanumeric keypad.

15. The device of claim 12 wherein said means for estimating further estimates the estimated dates of the second and third trimesters, and said means for displaying further displays the date of the woman's last menstrual cycle, and the estimated dates of the second and third trimesters.

16. The device of claim 12 further comprising timing means for generating signals corresponding to the current time and day, and said means for displaying further displays said current time and day on said display.

17. The device of claim 12 wherein said means for displaying further displays a standard calendar display.

18. The device of claim 12 wherein said means for storing further includes a standard fetal weight and height chart, and said means for displaying further displays the corresponding fetal weight and height for the estimated age of gestation.

19. The device of claim 12 wherein said means for estimating further estimates the date after which all pregnancy tests would tell a woman if she is pregnant, and said means for displaying displays that latter date.

20. The device of claim 12 wherein said means for estimating further estimates the weeks and dates that amniocentesis should be performed, and said means for displaying further displays those latter weeks and date.

21. The device of claim 12 wherein said means for estimating further estimates the date for the last possible day the woman can have an abortion, and said means for displaying displays said latter date.

* * * * *